United States Patent [19]

Spears

[11] Patent Number: 5,261,875
[45] Date of Patent: Nov. 16, 1993

[54] METHOD AND APPARATUS FOR INJECTION OF GAS HYDRATES

[75] Inventor: James R. Spears, Bloomfield Hills, Mich.

[73] Assignee: Wayne State University, Detroit, Mich.

[21] Appl. No.: 818,045

[22] Filed: Jan. 8, 1992

Related U.S. Application Data

[63] Continuation of Ser. No. 655,078, Feb. 14, 1991, Pat. No. 5,086,620.

[51] Int. Cl.$^5$ ............................................ A61M 37/00
[52] U.S. Cl. ................................. 604/24; 62/51.1; 604/101; 604/280; 606/194
[58] Field of Search ................... 604/96–103, 604/22–26, 264, 280, 282; 62/51.1, 78, 46.1; 128/658; 606/191, 192, 194

[56] References Cited

U.S. PATENT DOCUMENTS

| | | | |
|---|---|---|---|
| 2,975,606 | 3/1961 | Karwat | 62/46.1 |
| 3,459,565 | 8/1969 | Jones | |
| 3,963,503 | 6/1976 | Mackenzie | |
| 3,972,721 | 8/1976 | Hammel et al. | |
| 4,104,074 | 8/1978 | Rostoker | |
| 4,285,977 | 8/1981 | Yezek et al. | 62/46.1 |
| 4,303,432 | 12/1981 | Torobin | |
| 4,323,420 | 4/1982 | Masnari et al. | |
| 4,332,907 | 6/1982 | Vieli | |
| 4,332,908 | 6/1982 | Vieli | |
| 4,347,326 | 8/1982 | Iwami et al. | |
| 4,385,635 | 5/1983 | Ruiz | 128/658 |
| 4,572,203 | 2/1986 | Feinstein | |
| 4,573,476 | 3/1986 | Ruiz | 128/658 |
| 4,658,601 | 4/1987 | Burchell et al. | |
| 4,674,480 | 6/1987 | Lemelson | |
| 4,930,319 | 6/1990 | Bee et al. | 62/46.1 |
| 4,969,878 | 11/1990 | Schmidt et al. | 604/264 |
| 5,037,403 | 8/1991 | Garcia | 604/281 |
| 5,044,164 | 9/1991 | Bee | 62/46.1 |
| 5,086,620 | 2/1992 | Spears | 62/78 |
| 5,116,317 | 3/1992 | Carson, Jr. et al. | 604/96 |

OTHER PUBLICATIONS

Gas Hydrates of Nitrogen and Oxygen, II, 84 Recuil 1085 (1965), A. Van Cleeff and G. A. M. Diepen, pp. 1085–1093.

The ability of small molecules to form clathrate hydrates of structure II, D. W. Davidson, Y. P. Handa, C. I. Ratcliffe & J. S. Tse, Nature, vol. 311, pp. 142–143.

Structure of Oxygen Clathrate Hydrate by Neutron Powder Diffraction, J.S. Tse, U. P. Handa, and C. I. Ratcliffe, Journal of Inclusion Phenomena 4 (1986), pp. 235–240.

*Primary Examiner*—C. Fred Rosenbaum
*Assistant Examiner*—Chalin Smith
*Attorney, Agent, or Firm*—Brooks & Kushman

[57] ABSTRACT

A method of gasification of an environment having the characteristic of a low concentration of gas. The method is particularly suited for oxygenation of hypoxemic blood. The method comprises the steps of preparing a powdered oxygen hydrate; mixing the hydrate with powdered ice; pulverizing the mixture of the hydrate and the ice into small particles; encapsulating the mixture of the hydrate and the ice within a pressure vessel; applying a high pressure to the mixture; warming the pressure vessel and its contents to provide an aqueous suspension of the hydrate within liquid water formed from the ice upon warming; providing a conduit in communication with a catheter, the catheter having one or more high resistance exit ports; and intravenous injection of the suspension of particles at a rate which permits mixing of the hydrate with its environment before decomposition of the gas hydrate or bubble coalescence can occur.

21 Claims, 2 Drawing Sheets

METHOD AND APPARATUS FOR INJECTION OF GAS HYDRATES

CROSS-REFERENCE TO RELATED APPLICATION

This application is a continuation of my co-pending application Ser. No. 655,078, filed Feb. 14, 1991, now U.S. Pat. No. 5,086,620.

BACKGROUND OF THE INVENTION

1. Technical Field

This invention generally relates to a method and apparatus for injecting a gas hydrate into an environment of interest. More particularly, the invention concerns a method and apparatus for systemic oxygenation of hypoxemic blood by intravenous injection of an aqueous suspension of an oxygen clathrate hydrate.

2. Description Of Background Art

Oxygen administration by ventilation, even at a high inspired oxygen tension, may be ineffective in potentially reversible respiratory insufficiency in a clinical setting. Such conditions include adult respiratory distress syndrome, acute pulmonary edema, foreign body aspiration, pulmonary embolism, and respiratory distress syndrome of infancy. The problem of how to treat such conditions is compounded by the pulmonary toxicity that may result from prolonged exposure to relatively high inspired oxygen tensions.

Currently, the only potentially viable medical approach for systemic oxygenation of patients calls for use of an IVOX catheter. In such devices, gas exchange occurs at the interface of a membrane of multiple small tubules and blood in the inferior vena cava. Although the potential utility of such devices has been demonstrated clinically in a small number of patients, the large size of the catheter (7–10 mm diameter) which is inserted in the femoral vein, and the large surface area presented by the tubules may result in venous thrombosis and pulmonary embolism.

Entrapment of gases within liquids and solids is an important goal in many biologic and industrial processes. An example in biology is the uptake of oxygen by deoxyhemoglobin. In industry, gases are often used as foaming agents and are occasionally dissolved in fluids as reactants in chemical reactions. Various other examples include gasification of water for consumption, waste water management, and detoxification of hazardous wastes.

There are two commonly used means for gasification of liquid and solid media: 1) diffusion of gas into the media upon contact with its surface, and 2) injection of gas bubbles or of a gas-releasing precursor into the substance of the media. But diffusion is a relatively slow process. In order to inject bubbles into a medium to create a foam or to increase the surface area at a gas/medium interface, one can increase the rate of gas diffusion. However, it is often necessary to use a surfactant to reduce bubble surface tension so that sufficiently small and/or uniform bubbles can be produced. For certain applications, however, the presence of the surfactant is undesirable. Likewise, the breakdown products after liberation of a gas from a precursor may be problematic.

In the medical field, safe and effective oxygenation of hypoxemic blood (by intravascular injection of oxygen foam or an oxygen-liberating material) has not previously been achieved. Obstruction of capillaries by surfactant-stabilized foam, inadequate mixing with blood, or liberation of toxic breakdown byproducts (including toxic oxygen moieties) of an oxygen precursor would typically occur.

Accordingly, it is an object of the present invention to provide a means for injection of bubbles into a medium without the need for a surfactant.

It is a further object of the present invention to make the bubble size so small that mixing can be achieved rapidly, whereby excessive bubble coalescence and adherence between large numbers of bubbles do not occur.

In the case of oxygenation of blood, rather than using a foam, the need has arisen to inject a liquid suspension of microbubbles of a sonicated crystalloid solution without a surfactant or with a relatively biocompatible surfactant such as albumin. Certain techniques for encapsulating a hyperbaric gas for treatment with encapsulated gaseous precursors (such as microbubbles of oxygen) were disclosed in my co-pending U.S. patent application Ser. No. 655,078, which is herein incorporated by reference. The method disclosed therein includes the step of applying ultrasound energy to a probe disposed within an environment of a hyperbaric gas and an encapsulating material.

Previous approaches to the problems of delivering oxygen to hypoxemic blood, wherein a sonicated crystalloid solution is injected by a liquid suspension of microbubbles often produce an oxygen content which is insufficient to produce significant systemic oxygenation. For example, such approaches may only be capable of delivering less than 0.5 cc gas for each cc of the suspending fluid. To provide a desirable level of systemic oxygenation requires 50 to 300 cc oxygen/min. Therefore, it is another object of the present invention to provide a carrier for the gas-rich material, the carrier containing a volume of gas which is relatively small compared to the volume of gas delivered. Typically, a gas content of >10 cc gas per gram of injectate is desirable.

Additionally, the need has arisen for a method which permits intravenous oxygenation with a relatively small catheter (<2 mm). A commercially available ultrasound imaging guidance system allows rapid percutaneous insertion of catheters into the internal jugular vein, thereby permitting insertion of a suitable catheter into the right atrium or vena cavae within several minutes.

SUMMARY OF THE INVENTION

In accordance with the invention, a novel method and apparatus for intravenous injection of gas hydrates in an aqueous suspension is disclosed. A powdered gas hydrate is stabilized in a suspending aqueous carrier by application of external pressure in a manner which does not promote hydrate formation within the aqueous carrier. Upon ejection of the suspension of gas hydrate from pressurized apparatus, the fall in pressure surrounding the hydrate results in its decomposition. The aqueous carrier facilitates rapid ejection of the gas hydrate and adequate mixing in an environment (such as a blood vessel) external to the pressurized device, so that hydrate decomposition can be made to occur during and after mixing. As a result, microscopic and submicroscopic gas (oxygen-rich) bubbles generated during hydrate decomposition can be dispersed relatively uniformly, without using a surfactant, within the external environment.

In order to adequately inject oxygen hydrate particles intravenously, a liquid carrier is necessary. I have demonstrated the feasibility of using relatively gas-free water to stabilize oxygen hydrate particles at 0° C. under pressure. The coexistence of solid hydrate and gas-free liquid water (in contrast to water saturated with gas in equilibrium with a hydrate) is achievable because of differences in their temperature-pressure phase relationships. For example, increasing the external applied pressure depresses the freezing point of water in a linear manner to a minimum of −22° C. at 2 kbar, while application of similar pressure increases hydrate stability.

In practicing the invention, the broad process steps are:

1. preparation of oxygen clathrate hydrate powder;
2. preparation of gas-free water, such as a 5 g % dextrose solution, as a carrier of oxygen clathrate hydrate particles;
3. pulverization and filtration of a mixture of oxygen hydrate and gas-free ice powder; and
4. injection of a suspension of particles through high-pressure tubing and a catheter provided with one or more high resistance exit ports before decomposition into oxygen intravenous bubbles and a liquid carrier.

Other objects and advantages of the invention will become apparent upon reading the following detailed description and upon reference to the following drawings.

BRIEF DESCRIPTION OF THE DRAWINGS

FIG. 1 is a schematic diagram of apparatus used to practice a method according to the present invention of injecting a gas hydrate into an environment of interest;

FIG. 2 is a longitudinal sectional view of a catheter constructed in accordance with the present invention;

FIG. 3 is a transverse sectional view of the catheter according to the present invention taken along the line 3—3 of FIG. 2;

FIG. 4 is a transverse sectional view of the catheter according to the present invention taken along the line 4—4 of FIG. 2; and FIG. 5 is a schematic diagram of an alternate embodiment of the apparatus used to practice the method of the present invention.

BEST MODE(S) FOR CARRYING OUT THE INVENTION

With reference to FIGS. 1-5 of the drawings, the apparatus used to practice the disclosed method includes a suitable high pressure chamber 10, an on-line filter 26, high pressure tubing 14 modified to communicate with a catheter 16 with one or more high resistance exit port(s) 30, and mechanisms for control of temperature, pressure, and flow. I will first describe the method and then the apparatus used for injection of gas hydrates according to the present invention.

In greater detail, the preferred method steps involving practicing the present invention comprise:

1. Prepare a powdered gas hydrate.
2. Maintain the gas hydrate at a low temperature to ensure stability of the hydrate at 1 bar.
3. Mix the gas hydrate with powdered ice.
4. Pulverize and filter the mixture.
5. Place the hydrate/ice mixture in a pressure vessel.
6. Subject the mixture to a vacuum for several minutes to remove dead space gas between the hydrate/ice particles.
7. Apply pressure to the pressure vessel, so that the hydrate remains stable while the temperature of the vessel and its contents are increased to melt the ice, typically at temperatures in the −20° C. to +30° C. range.
8. Deliver the aqueous suspension of hydrate into an environment of interest by opening a valve which regulates a tubing connecting the vessel to the external environment.
9. Provide a high resistance exit port(s) within a catheter connected to the tubing so that sufficient pressure within the tubing is maintained for continued stabilization of the hydrate up to exit port(s).
10. Direct an ensuing stream of the aqueous hydrate suspension into the environment of interest at a rate which permits mixing of the hydrate with the environment to occur before full decomposition of the hydrate.

Preparation of Oxygen Clathrate Hydrate Powder

Turning first to FIG. 1 of the drawings, there is depicted a high pressure reaction vessel generally indicated by the reference numeral 10.

Water or 5 g % dextrose in water (5 DW) in a polypropylene tube is placed in the high pressure reactor vessel or bomb 10 (MRA-112R, 27 cc capacity, Leco Corp., Tem-Press Div., Bellefonte, Pa.; pressure rated for>75,000 psi). Standard fittings at one end of the vessel permit pressurization with gas or liquid media. At the opposite end of the vessel, a prototype titanium 3 mm tip probe is provided (Sonics and Ultrasonic Materials) with a cone seal incorporated at the node point. The cone seal allows closure of the vessel 10 but does affect probe function. The probe was driven at 20 kHz with a conventional transducer and power supply.

Initial tests have been performed with argon. The bomb 10 was pressurized to 1 to 4 kbar with a two stage gas intensifier (model GI-60-10, Leco), and the bomb 10 maintained at 0° C. in a temperature-controlled environment 12, such as an ice bath. Similarly to the method disclosed in my co-pending application Ser. No. 655,078, the tip of the probe (for simplicity, not shown in FIG. 1) was positioned at the gas-water interface. During a 30–60 sec. period of sonication at 0° C., the gas at high pressure was dispersed rapidly throughout the water. Pressures to 8 kbar (about 120,000 psi) were achieved by pressurizing a microreactor vessel (model 438R, Leco) to 2 kbar with argon while it was externally cooled to −196° C. in liquid nitrogen, isolating the vessel from the source of argon, and then allowing it to warm to 0° C. All experiments conducted at>0.5 kbar were performed with the bomb enclosed in an explosion-proof chamber which was made by lining all sides of a conventional hood with 1/16 in. steel plates lined with ½ in. plywood.

After external cooling of the vessel (e.g., with liquid nitrogen), the hydrate was removed and its gas content determined by placing 1–2 grams in a closed syringe. Each technique produced a hydrate with a gas yield (STP) of>60 cc/g.

Having demonstrated the feasibility of gas hydrate formation with argon by sonication at elevated pressure, oxygen was then used with modification. All components were oil free. The gas intensifier was used to pressurize the reactor vessel 10 to 0.2 to 0.5 kbar while it was externally cooled with liquid nitrogen. After isolating the vessel from the intensifier and allowing it to warm to 0° C. in an ice bath 12, sonication at 20 kHz was performed for 30–60 sec at 1–4 kbar. The vessel was then cooled with liquid nitrogen and the hydrate removed.

The gas content was similar to that for argon, i.e., 60–70 cc/g.

Alternatively, the oxygen hydrate can be prepared in a conventional manner consisting of exposure of powdered ice in a pressure vessel, such as a Parr bomb, at −20° C. to −30° C. to oxygen at 2500 psi or greater for a prolonged period, during which time mixing of the powder is performed. The oxygen hydrate is then removed from the pressure vessel after cooling the vessel with liquid nitrogen.

II. Preparation of Gas-Free Water As A Carrier Of Oxygen Clathrate Hydrate Particles Intravenous infusion of oxygen hydrate powder is difficult without a liquid carrier. Although techniques exist in industry for transport of powdered materials without a liquid carrier, many problems still require solution. Among these include aggregation of particles, injection of dead space gas between particles, and the inability to inject particles with sufficient velocity into blood to achieve adequate mixing before bubble coalescence.

Under carefully controlled conditions, water may be a suitable carrier. Gas hydrates are in equilibrium with water saturated with gas at specific combinations of pressure and temperature. However, the relative amount of hydrate formed and the particle size produced is quite difficult to control. Equally importantly, intravenous injection of water saturated with gas at high pressure results in the production of large (>50 micron) bubbles and foaming.

Air hydrate crystals are stabilized by ordinary ice within which the crystals are embedded in deep ice cores. Under similar conditions, relatively gas-free liquid water can be used to stabilize oxygen hydrate near 0° C. by application of sufficient pressure.

The stability of oxygen hydrate particles suspended in relatively gas-free liquid water was demonstrated as follows. Powdered oxygen hydrate with a gas content of about 100 cc/g was prepared in a Parr bomb, as described above. Teflon tubes (i.d. 8 mm), which had been sealed at one end by heat shrinking onto cylindrical glass plugs, were filled with a 2:1 mixture of powdered gas-free 5 g % dextrose in water and oxygen hydrate. Deoxyhemoglobin 5 g % (rabbit) had been dissolved in the D5W before preparation of the powdered ice. A temperature of −100° C. was maintained during filling of the tubes by immersing them in ethanol which had been cooled with liquid nitrogen to a temperature close to its freezing point. The opposite end of each tube was also sealed by heat shrinking the tubing onto the distal end of a long (>4 cm) glass plug. Care was taken to ensure that the proximal end of the plug was kept at −100° C. to prevent decomposition of the oxygen hydrate. The total volume of powdered hydrate was about 0.5 cc per tube.

The tubes were placed in the high pressure reaction vessel 10 (Leco), pre-cooled to <−80° C. and the remaining volume of the vessel filled with ethanol at −80° C. After vessel closure, hydraulic compression with ethanol to 1 kbar was provided with a model PG-100-HPC pressure generator 20 (Leco, 100,000 psi max. pressure), consisting of a differential area piston 24 driven by a hydraulic pump (not shown). The vessel temperature was allowed to equilibrate with a 0° C. ice bath for 4 hours.

The vessel was then cooled externally to <−100° C. with liquid nitrogen, and the tubes were removed after reducing the pressure to 1 bar. That melting of the ice at 0° C. in the bomb 10 under pressure had occurred was evident by the translucent appearance of the ice and by the flattened appearance of the tubes. Scattered throughout the translucent ice were white particles, consistent with hydrate stability. Oxygenation of the deoxyhemoglobin did not occur; i.e., oxygen diffusion from the hydrate to the gas-free liquid water was not evident.

The fact that there was insufficient oxygen lost from the hydrate to the liquid phase of the ordinary water to oxygenate a dilute solution of hemoglobin shows that stabilization of oxygen hydrate at 0° C. occurred by application of suitable pressure with relatively gas-free liquid water.

III. Pulverization And Filtration Of Oxygen Hydrate

At 1 bar, oxygen clathrate hydrate is quite stable when kept at −196° C. under liquid nitrogen. The gas yield per gram was found to be unchanged for samples (prepared in a Parr bomb) which were stored for 4 months in a Dewar container filled with liquid nitrogen (1 bar). In addition, the gas yield/g was also unaffected by pulverization—either manually with a steel mortar and pestle or mechanically with a rotary blade grinder—when temperatures approaching −196° C. were employed.

After grinding by either approach, the particles were filtered through either a 400 mesh copper screen (38 micron pore size) or sintered stainless steel filters (Mott) with pore sizes of either 2, 5, or 20 microns. Filtration was performed under liquid nitrogen in each case.

In order to examine the potential effect of hydrate particle size and resultant bubble size upon decomposition of the hydrate, the particles were initially suspended in cold ethanol (−100° C.), and the suspension was applied to the surface of ethanol at room temperature. Both a light microscope and a stereo microscope (Reichart) were used with either a Sanyo CCD video camera at 1/1000 sec shutter speed or a Pulnix (Advanced Technology Div.) CCD video camera at 1/1800 sec shutter speed to record bubble generation on a ¾ in videotape recorder (Sony). When unfiltered particles were used, the mean bubble size was roughly 30 to 50 microns within a 10 to 150 micron range. Particles filtered through the 38 micron filter produced bubbles with a mean size of roughly 20 micron. No bubbles >50 micron were noted.

Oxygen hydrate particles, both filtered and unfiltered in separate runs, were mixed with degassed D5W ice particles in a 1:5 to 1:10 volume ratio under liquid nitrogen. After packing the mixture of powdered hydrate and D5W in one end of a 13 mm diameter vessel at near liquid nitrogen temperature, a vacuum was applied to the vessel with a vacuum pump (model DD90), Precision Scientific, Chicago,; min. pressure $3 \times 10^{-4}$ torr) for 10 minutes. The same pump has been used to degas the D5W.

The purpose of the vacuum was to eliminate dead space gas within the powder. The bomb was then pressurized with degassed water at 0° C. via the hydraulic compressor to 1 kbar. A steel cylinder with a rubber gasket which moves with the application of pressure within the vessel cavity contacted the powder directly to reduce mixing between the powder and the water from the compressor. Premature contact of liquid water at 0° C. with the hydrate before a pressure of >150 bar was applied would otherwise risk decomposition of the hydrate.

The distal end of high pressure tubing 14 (1/16 in. o.d., 1/64 in. i.d.) was crimped to reduce flow to <1 cc/min at a pressure of 1 kbar at 0° C. The latter temperature was achieved by allowing the vessel 10 and tubing 14 to warm in an ice bath for at least 1 hour before attempting to eject fluid from the tubing. Once a valve 22 between the vessel 10 and the tubing 14 was opened, pressure in the tubing was essentially the same as in the vessel, thereby promoting hydrate stability before exiting the tubing.

Video recordings of injection of the hydrate into room temperature water demonstrated marked differences between bubble size depending upon whether filtered or unfiltered hydrate particles were used, similar to the results when cold ethanol was used to stabilize the hydrate.

In the present invention, an aqueous suspension of a gas hydrate is used for intravenous injection. Gas hydrates are clathrates, i.e., inclusion materials wherein one or more molecular guest species are physically trapped within the molecular cages of a host. Clathrate hydrates consist of polyhedral frameworks of hydrogen-bonded water molecules forming cages on the order of 7 to 10 angstroms in diameter. The polyhedral frameworks of water are comprised of typically either 12, 46, or 136 water molecules, within the cages of which are trapped guest molecules (usually one at the center of each cage). The 46 $H_2O$ polyhedron has 6 cages of one size and 2 others slightly smaller, while the 136 $H_2O$ polyhedron has 8 larger and 16 smaller cages. No chemical bonding occurs between the gas molecules trapped within the cages and the hydrate lattice. Rather, individual gas molecules are physically trapped within the cages formed by water molecules.

Gas hydrates are "true clathrates" in that the entrapped molecular species do not form hydrogen bonds with or replace a component of the tetrahedrally coordinated framework of strongly hydrogen-bonded oxygen atoms of the water molecule. The guest gas molecules interact with the water lattice structure only through weak (van der Waals) dispersion forces. The lattice structure of gas hydrates of small guest molecules, including oxygen, consists of 16 small cavities and 8 large cavities formed by 136 water molecules. Oxygen atoms of the latter form pentagonal dodecahedra (12 pentagons arranged spherically) for the small cavities and hexakaidecahedron (12 pentagon plus 4 hexagons arranged spherically) for the large cavities. The 0.5 nm and 0.7 nm diameters of the small and large cavities permit the occupancy of one oxygen molecule (0.4 nm diameter) per cavity.

The presence of gas during crystallization stabilizes the cavities, and the well formed cavities distinguish gas hydrates from ice polymorphs. The composition of the gas hydrate with all cavities filled is a 1:5.7 molar ratio of oxygen:water. The quantity of oxygen gas which could be liberated from the hydrate is in the range of 70 cc to 200 cc (STP) per gram of hydrate.

When cage occupancy of oxygen within the hydrate approaches 100%, the gas yield upon decomposition is >100 cc gas/g hydrate at standard temperature and pressure.

The phase diagram involving hydrate, ice, gas, and liquid water phases for oxygen is such that either high pressures or low temperatures are required to prevent decomposition of oxygen hydrate. For example, a pressure of >120 bar is required at 0° C. The pressure required for hydrate stability rapidly increases with higher temperatures.

A mixture of hydrate suspended in liquid water exists at a variety of pressure/temperature combinations. Injection of such a suspension into a medium such as blood would be problematic because liquid water may be supersaturated with oxygen. At a minimum pressure of 120 bar at 0° C., approximately 6 cc of gas would be liberated explosively (with the production of large bubbles) per gram of liquid, given the solubility of oxygen in water, upon exposure of the liquid to 1 bar.

Figure 5:
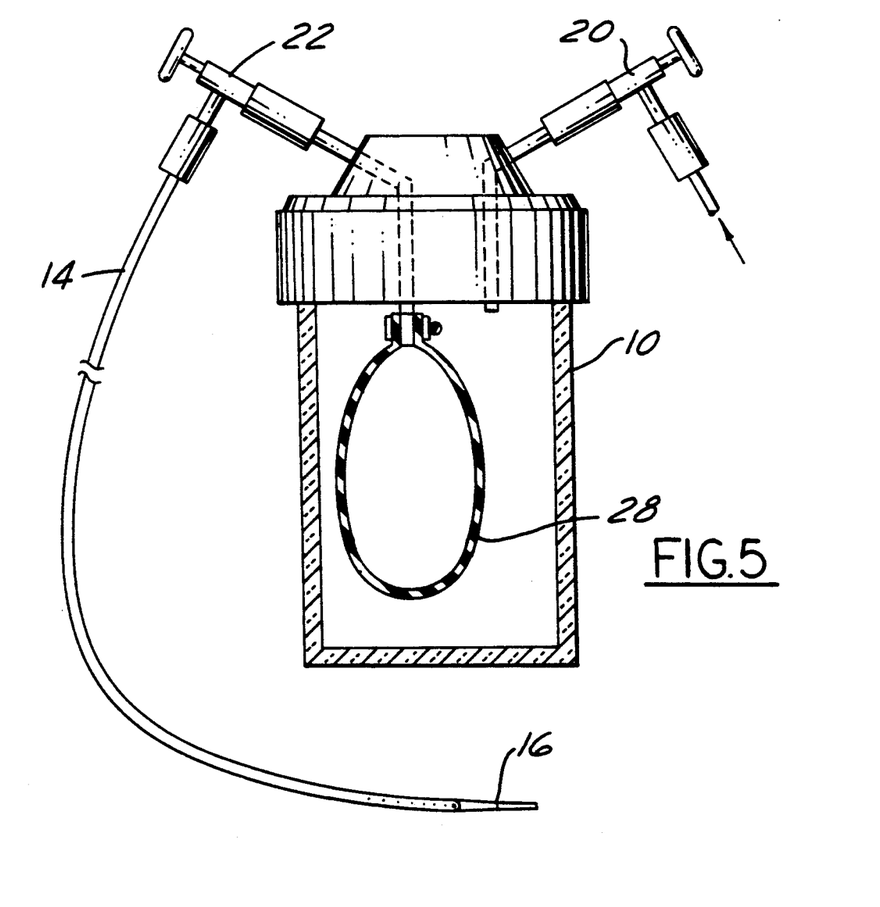

An alternative high pressure vessel is depicted in FIG. 5. In that embodiment the hydrate/ice mixture is placed in a pressure chamber or gas-impermeable, compressible reservoir 28 within the pressure vessel 10. The dead space or voids between powder granules can be filled with carbon dioxide, which is highly soluble in water. Alternatively, a vacuum can be applied to degas the voids between granules. Adequate non-gaseous compression of the powdered mixture prior to placement of the mixture in the reservoir eliminates most of the dead space between granules, thereby greatly reducing the need for the above-described use of carbon dioxide or a vacuum.

When a pressure >120 bar is applied to fluid, by movement of either liquid or gas into the pressure chamber 10, the hydrate can be warmed to approximately 0° C. without decomposition. Simultaneously, the ice melts because of the freezing point depression effect of pressure (approximately −1° C./100 bar).

Unlike decomposition of water supersaturated with gas, decomposition of the hydrate upon relief from a high pressure environment into a medium at 1 bar is not instantaneous. At 37° C. and 1 bar, several hundred milliseconds are required before most of the hydrate decomposes. If the velocity of injection is made sufficiently great to ensure adequate mixing of the hydrate suspension with a medium such as blood (e.g., similar to rates used during injection of contrast media in clinical angiographic procedures), then mixing occurs before a significant fraction of the hydrate has decomposed or before bubble coalescence occurs.

The liquid water carrier for the hydrate has an insufficient gas concentration to result in uncontrolled and relatively large bubble formation. Thus, virtually all the gas released is derived from the hydrate, and the present invention allows the use of a gas hydrate particle to be used as a bubble. The rate of hemoglobin binding to the oxygen in the microscopic (or smaller) bubbles is extremely rapid, so that the bubbles will disappear well before encountering pulmonary capillaries.

The high pressure tubing 14 communicates with a catheter 16. Maintenance of internal catheter temperature near 0° C. after in vivo placement is possible, and maintenance of appropriate pressure (e.g., >150 bar) within a high pressure stainless steel tubing modified into a catheter is achievable by the use of high resistance exit ports 30 (FIGS. 2–4), through which the aqueous suspension of hydrate particles pass before mixing with venous blood. Decomposition of the hydrate particles occurs only after injection. Considering that 5 cc boluses of iced saline are routinely injected into the right atrium without adverse clinical effects for measurement of cardiac output, use of a temperature of 0° C. for injection of the hydrate particles will be well tolerated.

In the preferred embodiment of the invention (FIG. 2), the distal end of the tubing 14 is incorporated in the catheter system 16. In addition to an elongated cylindrical tube with exit ports 30 for injection of the hydrate suspension, a conduit 32 is provided for monitoring pressure in blood (such as the right atrial pressure), and an additional lumen 36 is provided for inflation of balloons 38, 40 positioned proximal and distal to the exit ports 30. Inflation of the balloons 38, 40 ensures that the supporting walls 42, 44 of a central vein or cardiac chamber are not immediately adjacent to the exit ports 30 of the catheter.

Figure 1:
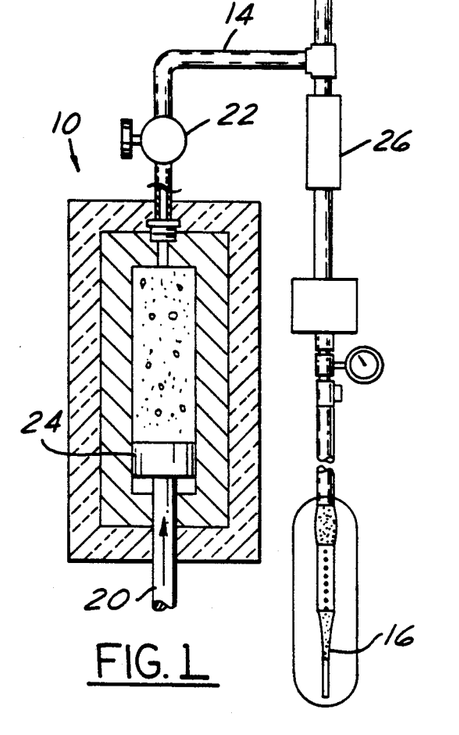
Figure 2:
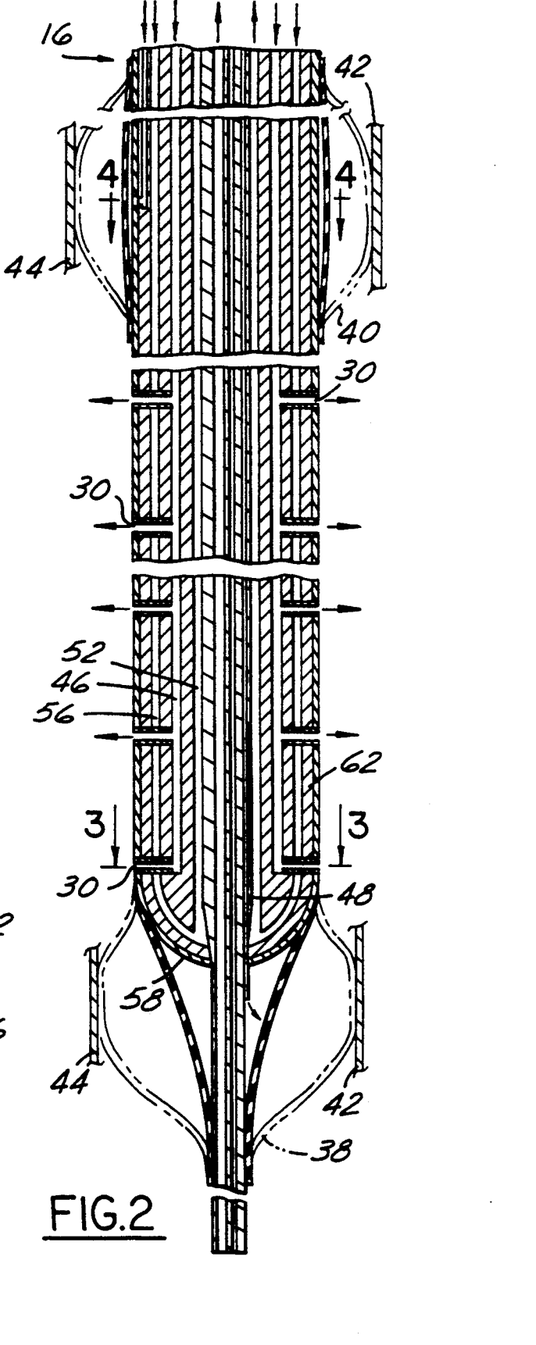

A fiberoptic is disposed within the lumen 34 for on-line continuous monitoring of oxygen saturation and/or pressure. The fiberoptic is used as a feedback to regulate the volume of hydrate suspension injected.

Figure 3:
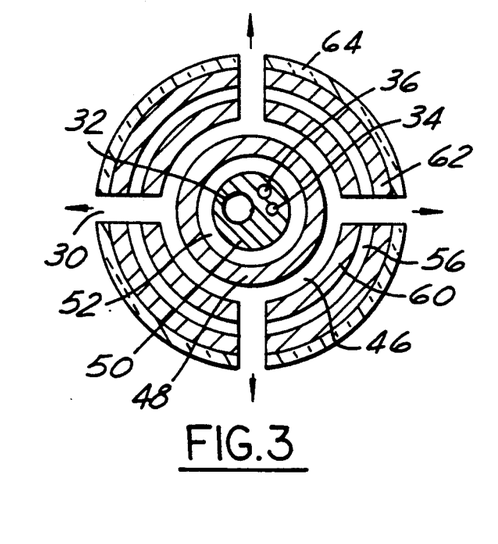
Figure 4:
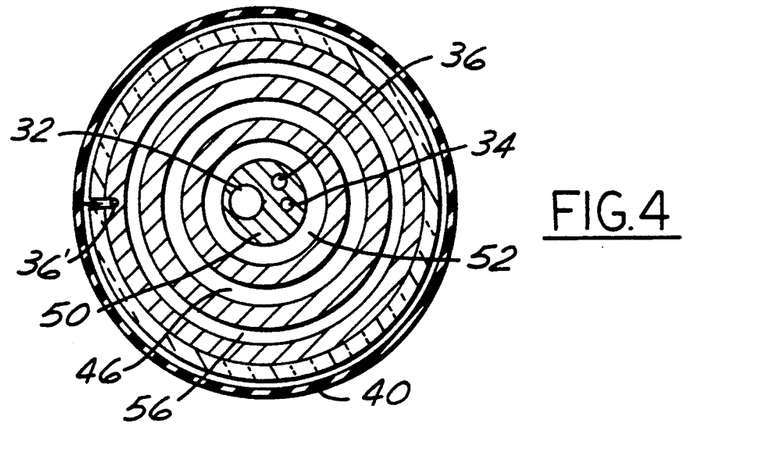

Turning now with particular attention to FIGS. 2–4, additional detail of the catheter 16 will be disclosed. As illustrated, the catheter 16 comprises an elongated cylindrical tube defining a channel 46 for ducting a fluid under high pressure. In communication with the channel 46 are one or more exit ports 30 extending transversely from the channel 46 through the cylindrical tube 16. The exit ports 30 have a diameter which is sufficiently small to provide resistance to the fluid upon its passage therethrough. In this way, the high pressure to which the fluid is subjected in the channel 46 continues as the fluid enters the exit ports 30.

Referring now primarily to FIG. 3, it is apparent that the elongated cylindrical tube 60 encloses an inner tube 48 which extends axially along the channel 46. The inner tube 48 encloses the first lumen 34 for housing a fiberoptic device, and a second lumen 36 for communicating a pressure source to the balloons 38, 40 which are mounted on the outside of the catheter. The first and second lumens 34, 36 are defined within and separated by an axially extending core 50.

The core 50 and the inner tube 48 define therebetween an annular inner cooling channel 52 for ducting a cooling fluid which is in thermal communication with the channel 46 extending along the inner tube 48.

An outer cylindrical tube 62 encloses the elongated cylindrical tube 60. Those tubes 60, 62 define therebetween an annular outer cooling channel 56 for abducting a cooling fluid which is also in thermal communication with the channel 46 through which the injectate is delivered through the exit ports 30.

As indicated in FIG. 2, the outer cylindrical tube 62 defines at its distal end a rounded tip 58 which merges with the inner tube 48 so that the inner and outer cooling channels 52, 56 unite at the distal end of the outer cylindrical tube 54. In this way, a continuous cooling channel is provided because cooling fluid may flow uninterruptedly between the inner and outer cooling channels 52, 56.

Turning now with particular reference to FIG. 4, there is depicted in an uninflated condition the balloon 40 which is mounted at the proximal end of the catheter 16. Also illustrated in FIG. 4 is the second lumen 36' for inflating the associated distal balloon. When the balloons 38, 40 are inflated through lumens 36, 36', they are urged between the walls 42, 44 of the blood vessel into which the catheter 16 has been positioned. Upon inflation, the catheter 16 is supported between the walls 42, 44 so that there is no direct contact between effluent from the high resistance exit ports 30 and the walls 42, 44.

It will be apparent that a thermally insulating cylindrical outer sleeve 64 (FIG. 3) can be provided if desired.

A modification of the catheter design consists of a single exit port 30 positioned at the distal end of the catheter. The single exit port 30 functions as a nozzle, so that the oxygen hydrate suspension is sprayed in multiple directions, thereby facilitating mixing of the suspension with blood.

When oxygen saturation in blood (measured either with the catheter 16, a second oxygen saturation monitoring catheter in the pulmonary artery, or with an ear or finger oximeter) approaches a value in the 90–95% range, for example, as a result of injection of the hydrate, injection will be slowed in order to avoid excessive oxygen delivery, which would be associated with large bubble formation. The size of gas bubbles liberated upon decomposition of the hydrate depends on the size of the hydrate particle and its oxygen content. For example, a 0.2 um particle entrapping 100 cc O2/g hydrate will expand to a 0.9 um bubble at STP, since volume is a cubed function of diameter (however, the surface tension of water at this small dimension may reduce this diameter somewhat). A bubble of this dimension will disappear by dissolution in water within microseconds. Moreover, the extremely rapid binding of oxygen to deoxyhemoglobin may also help to ensure that insufficient time exists for bubble coalescence to occur.

The primary problem presented by excessive bubble coalescence, of course, would be foaming with resultant occlusion of pulmonary arterioles. Thus, it is important to determine whether a suitable combination of hydrate particle size and rate of injection exists for a given blood flow rate of hypoxemic blood, which would markedly improve blood oxygenation without also producing significant bubble coalescence. When such a combination is found for a given patient, injection of an appropriate amount of hydrate particles may be achievable with automatic feedback control provided by continuous on-line monitoring of oxygen saturation either in the pulmonary artery or possibly peripherally. Since the particle size can be fabricated as small as several nanometers, the bubble size of a decomposed particle (STP) of a hydrate in which all molecular cages are filled with oxygen bubbles can be made to be substantially less than a micron.

Accordingly, the method employs the use of small (e.g., <10 micron) particles of oxygen clathrate hydrate suspended in ordinary crystalloids, such as 5 g % dextrose in water (D5W). Since the hydrate can be fabricated from oxygen and D5W, the injectate consists solely of these two materials. The method of intravenous systemic oxygenation with oxygen clathrate hydrate particles is both safe and effective.

The product of the invention can be used as a foaming agent. The lack of need of a surfactant, the small size of the bubbles achievable, and the potentially inert nature of the product of the invention are useful features. For example, injection of a gas hydrate suspension into molten glass could be used to prepare a foamed glass in which the bubbles are smaller than the wavelength of visible light, so that the glass would retain its translucent appearance. The foamed glass preparation would be useful as thermal insulation in homes and buildings and would represent an improvement over conventional windows. Other high temperature applications would include injection of the suspension of gas hydrate into molten metals and polymers in order to reduce their density, modify their structural characteristics, porosity, etc.

Another application of the product in industry is the detoxification of hazardous waste. The oxygen hydrate in aqueous suspension provides a safe, easily handled high concentration of oxygen in water without the need for a gaseous source of high pressure oxygen to provide an equivalent concentration of the gas.

At high temperatures, most surfactants burn and would leave an undesirable residue in the material of interest. With the use of an appropriate gas hydrate (for some applications, an inert gas such as argon would be used), the hydrate suspension would simply be transformed to steam and inert gas. The steam would dissipate in large expanding bubbles or could be filtered from a medium containing small bubbles produced by gas liberated from the hydrate. In addition, the cooling effect of the steam could be used to increase the viscosity of the medium of interest simultaneously with its gasification, thereby inhibiting coalescence of bubbles liberated from the gas hydrate.

Among the technical challenges addressed by this invention are the preparation of oxygen hydrate particles of specified size; stabilization of oxygen hydrate with the use of relatively gas-free liquid water under pressure; control of temperature and pressure to prevent premature oxygen hydrate decomposition; and catheter development including fabrication of suitable high resistance exit ports. Intravenous administration of oxygen hydrate particles provides a practical means for systemic oxygenation of patients, possibly for many days, when ventilation alone is inadequate in the treatment of potentially reversible respiratory insufficiency.

What is claimed is:

1. A method of gasification of an environment of interest having the characteristic of a low concentration of gas, comprising the steps of:
   preparing a powdered gas hydrate;
   mixing the hydrate with powdered ice which has a low concentration of a dissolved gas;
   pulverizing the mixture of the hydrate and the ice into small particles;
   encapsulating the mixture of the hydrate and the ice within a pressure vessel;
   applying a high pressure to the mixture;
   warming the pressure vessel and its contents to provide an aqueous suspension of the hydrate within liquid water formed from the ice upon warming;
   providing a conduit in communication with the pressure vessel and a catheter, the catheter having one or more high resistance exit ports so that sufficient pressure is maintained for continued stabilization of the hydrate prior to emerging from the catheter; and
   injecting the suspension of the particles into the environment of interest at a rate which permits mixing of the hydrate with the environment before decomposition of the gas hydrate or bubble coalescence can occur.

2. The method of claim 1, further comprising the step of maintaining the hydrate at a low temperature to ensure stability of the hydrate prior to application of pressure.

3. The method of claim 2, wherein the step of maintaining the hydrate at a low temperature comprises maintaining the hydrate at a temperature below about $-100°$ C.

4. The method of claim 1, wherein the step of encapsulating the mixture of the hydrate and ice is followed by the step of applying a vacuum to the mixture of the hydrate and ice, prior to application of pressure, to remove dead space gas within the powdered mixture.

5. The method of claim 1, wherein the step of applying a high pressure is performed at pressures in excess of about 120 bar.

6. The method of claim 1, wherein the warming step is performed at temperatures between about $-20°$ C. and $+30°$ C.

7. The method of claim 1, wherein the gas hydrate comprises oxygen hydrate.

8. The method of claim 1, wherein the gas hydrate comprises oxygen clathrate hydrate.

9. The method of claim 1, wherein the gas hydrate comprises inert gas.

10. The method of claim 1, wherein the environment of interest comprises hypoxemic blood.

11. The method of claim 1, wherein the environment of interest comprises hazardous waste material.

12. The method of claim 1, wherein the environment of interest comprises a liquid glass.

13. The method of claim 1, wherein the environment of interest comprises a polymer.

14. The method of claim 1, wherein the environment of interest comprises a liquid metal.

15. A method of oxygenation of hypoxemic blood, comprising the steps of:
    preparing a powdered oxygen hydrate;
    mixing the hydrate with powdered ice which has a low concentration of a dissolved gas;
    pulverizing the mixture of the hydrate and the ice into small particles;
    encapsulating the mixture of the hydrate and the ice by sonication within a pressure vessel;
    subjecting the mixture to a vacuum to remove dead space within the powdered hydrate/ice mixture;
    applying a high pressure to the mixture;
    warming the pressure vessel and its contents to provide an aqueous suspension of the hydrate within liquid water formed from the ice upon warming;
    providing a conduit in communication with the pressure vessel and a catheter, the catheter having one or more high resistance exit ports so that sufficient pressure is maintained for continued stabilization of the hydrate prior to emerging from the catheter; and
    injecting a suspension of the particles into blood at a rate which permits mixing of the hydrate with the blood before decomposition or bubble coalescence can occur.

16. A catheter comprising:
    an elongated cylindrical tube defining a channel for ducting a fluid stream under high pressure;
    one or more exit extending transversely from the channel through the tube, the exit ports each having a diameter which is sufficiently small and a length adequate to convert the fluid stream into spray upon fluid passage therethrough, so that the high pressure to which the fluid is subjected in the channel reduces as the fluid exits the one or more ports and so that the spray may mix with the blood before said spray can decompose or bubbles within said spray can coalesce.

17. The catheter of claim 16 comprising:

a pair of balloons mounted on the catheter proximal and distal to the one or more exit ports, wherein the elongated cylindrical tube encloses an inner tube extending axially along the channel, the inner tube enclosing a first lumen for housing a fiberoptic device;

a second lumen for communicating a pressure source to the balloon mounted on the catheter;

the first and second lumens being defined within and separated by an axially extending core.

18. The catheter of claim 17, wherein:

the core and the inner tube define therebetween an annular inner cooling channel for ducting a cooling fluid which is in thermal communication with the channel extending along the inner tube.

19. The catheter of claim 18, further comprising:

an outer cylindrical tube which encloses the elongated cylindrical tube, the outer cylindrical tube and the elongated cylindrical tube defining therebetween an annular outer cooling channel for ducting a cooling fluid which is in thermal communication with the channel extending along the inner tube.

20. The catheter of claim 19, wherein the outer cylindrical tube defines at its distal end a rounded tip which merges with the inner tube so that inner and outer cooling channels unite at the distal end of the outer cylindrical tube, thereby enabling the cooling fluid to flow between the inner and outer cooling channels.

21. A catheter comprising:

an elongated cylindrical tube defining a channel for transporting a hydrate suspension under high pressure which is injected into the blood stream;

a single high resistance exit port for dispersion of the hydrate suspension in multiple directions so that the hydrate suspension may mix with the blood before decomposition or bubble coalescence can occur, said exit port having a diameter which is sufficiently small and a length adequate to reduce the high pressure to which said hydrate suspension is subjected in the channel and to convert said hydrate suspension into spray upon passage of suspension therethrough.

* * * * *

UNITED STATES PATENT AND TRADEMARK OFFICE
CERTIFICATE OF CORRECTION

PATENT NO. : 5,261,875

DATED : November 16, 1993

INVENTOR(S) : James Richard Spears

It is certified that error appears in the above-indentified patent and that said Letters Patent is hereby corrected as shown below:

Column 1, line 12:
Directly below the title "BACKGROUND OF THE INVENTION" and before the sub-title "1. Technical Field" insert the following language:

--This invention was made with Government support, under Contract No. R01 HL 33252, awarded by the National Institutes of Health. The Government has certain rights in the invention.--

Signed and Sealed this

Eighteenth Day of April, 1995

Attest:

BRUCE LEHMAN

*Attesting Officer*

*Commissioner of Patents and Trademarks*